(12) United States Patent
Suib et al.

(10) Patent No.: US 6,486,357 B2
(45) Date of Patent: Nov. 26, 2002

(54) CATALYTIC OXIDATION OF ALCOHOLS USING MANGANESE OXIDES

(75) Inventors: Steven L. Suib, Storrs, CT (US); Young Chan Son, Storrs, CT (US); Amy R. Howell, Tolland, CT (US)

(73) Assignee: The University of Connecticut, Storrs, CT (US)

( * ) Notice: Subject to any disclaimer, the term of this patent is extended or adjusted under 35 U.S.C. 154(b) by 0 days.

(21) Appl. No.: 09/929,302

(22) Filed: Aug. 14, 2001

(65) Prior Publication Data

US 2002/0128506 A1 Sep. 12, 2002

Related U.S. Application Data

(60) Provisional application No. 60/225,481, filed on Aug. 15, 2000.

(51) Int. Cl.[7] .............................................. C07C 45/29
(52) U.S. Cl. ..................... 568/320; 568/322; 568/360; 568/363; 568/402; 568/431; 568/471; 568/480
(58) Field of Search ............................... 568/320, 322, 568/360, 363, 402, 431, 471, 480

(56) References Cited

U.S. PATENT DOCUMENTS

| 5,340,562 A |   | 8/1994  | O'Young et al. ............ 423/599 |
|-------------|---|---------|-------------------------------------|
| 5,523,509 A | * | 6/1996  | O'Young et al.                      |
| 5,695,618 A |   | 12/1997 | O'Young et al. ...... 204/157.43    |
| 5,912,388 A | * | 6/1999  | Urch et al.                         |
| 6,020,533 A | * | 2/2000  | Lewis et al.                        |

OTHER PUBLICATIONS

M. E. Davis, "New Vistas in Zeolite and Molecular Sieve Catalysis" *Acc. Chem. Res.* 1993, 26, 111–115.
I. W. C. E. Arends, et al., "Oxidative Transformations of Organic Compounds Mediated by Redox Molecular Sieves" *Angew. Chem. Int. Ed., Engl.* 1997, 1144–1163.
R. N. DeGuzman, et al., Synthesis and Characterization of Octahedral Molecular Sieves (OMS–2) Having the Hollandite Structure, *Chem. Mater.* 1994, 6, 815–821.
Y.C. Son, et al., "Efficient, Catalytic, Aerobic Oxidation of Alcohols with Octahedral Molecular Sieves", *Angew. Chem. Int. Ed.* 2001, 40, No. 22.

H. Heineman, *Catalysis Reviews Science and Engineering*, 28(2&3), 185–264 (1986).
R. M. Dessau, "Shape–Selective Reactions of Zeolites. Selective Metal–Catalyst Hydrogenation and Oxidation Using ZSM–5" *J. Cataly.*, 1982, 77. 304.
C–L O'Young, et al., Micropore size distribution of octahedral molecular sieves (OMS), *Microporous Materials* 11, 1997, 1–8.
P. B. Venuto, "Organic catalysis over zeolites; a perspective on reaction paths within micropores," *Microporous Materials 2*, 1994, 297–411.
C. W. Jones, et al., "Organic–functionalized molecular sieves as shape–selective catalysts", *Chemical Engineer, Nature*, 1998, 393.
M. Hudlicky, *Oxidations in Organic Chemistry*, ACS, Washington, DC, 1990, pp. 1–14; 26–37; 114–126; 132–149; 174–182.
C. Song, et al., "Shape–selective alkylation of naphthalene with isopropanol over moredenite catalysts", *Microporous Materials 2*, 1994, 467–476.
Y. Yoshinaga, et al., "Shape–Selective Hydrogenation and Oxidation over a Platinum–Containing Ultramicroporous Heteropolyoxometallic Compound", *Angew. Chem. Int. Ed. Engl.*, 1997, 36, 2833.
C. F. Martens, et al., "Shape–Selective Oxidation of Benzylic Alcohols by a Receptor Functionalized with Dicopper(II) Pyrazole Complex", *Am. Chem. Soc.*, 1994, 116, 5667.
H. B. Friedrich, et al., "The efficient and selective oxidation of alchols with zeolite NaY–supported sodium ruthenate", *J. Mol. Catal. A: Chem.*, 2000, 160, 401.
J. Luo, et al., "Total oxidationof volatile organic compounds with hydrophobic cryptomelane–type octahedral molecular sieves", *Microporous Material.*, 2000, 35, 209.

* cited by examiner

*Primary Examiner*—James O. Wilson
*Assistant Examiner*—Sikarl A. Witherspoon
(74) *Attorney, Agent, or Firm*—Cantor Colburn LLP

(57) ABSTRACT

A method of oxidizing an organic alcohol, wherein the organic alcohol is contacted with a stoichiometric excess of oxygen in the presence of an effective catalytic amount of a maganese-containing octahedral molecular sieve or octahedral layer. Primary alcohols are selectively oxidized to aldehydes, and secondary alcohols are selectively oxidized to ketones.

23 Claims, 2 Drawing Sheets

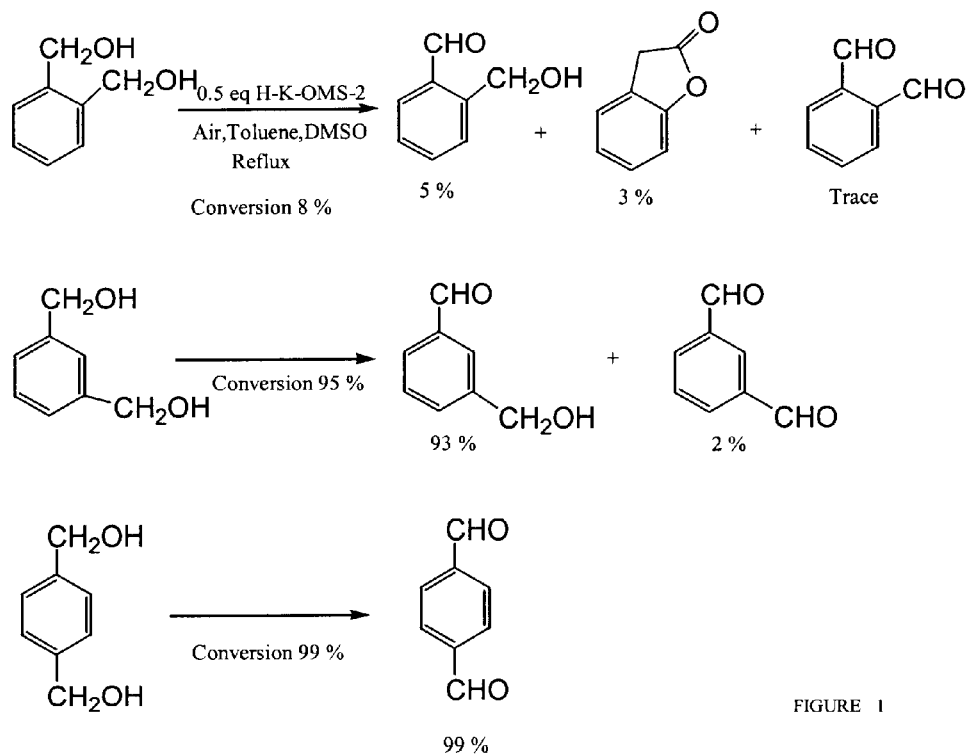
FIGURE 1
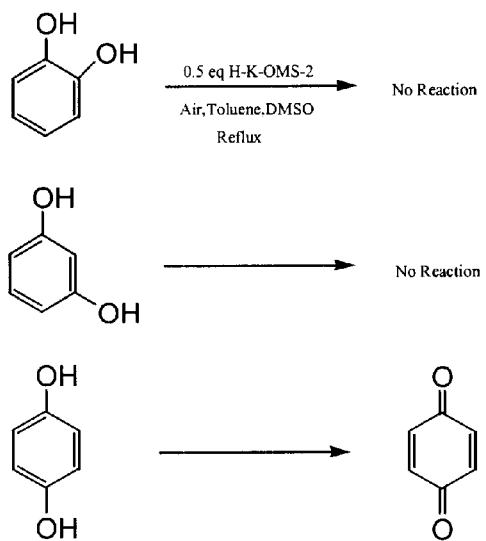
FIGRE 2

CATALYTIC OXIDATION OF ALCOHOLS USING MANGANESE OXIDES

This application claims the benefit of No. 60/225,481 filed Aug. 15, 2000.

BACKGROUND

This invention relates to a method for the catalytic oxidation of alcohols, and in particular, to a method for the selective oxidation of alcohols catalyzed by manganese oxides.

The oxidation of alcohols to carbonyl compounds is of great interest to academia and industry, particularly the fine chemicals industry. A number of catalytic oxidations of alcohols in which oxygen is the secondary oxidant have been reported, using ruthenium, cobalt, copper, palladium, and platinum metal catalysts with additives such as potassium carbonate, sodium bicarbonate, pyridine, molecular sieves, and phenanthroline.

Stoichiometric metal oxidants such as chromium (VI) compounds and active manganese dioxide have also been widely used, particularly for the oxidation of allylic and benzylic oxidations. The reactivity of active manganese oxide is inconsistent, depending on preparation methods, compositions, and structure. Complicated preparation methods are often necessary, and the use of freshly made active manganese oxide is required. Moreover, five to fifty equivalents of these reagents are required to obtain oxidation products, resulting in large amounts of non-reusable, toxic waste. Use of peroxides gives rise to handling hazards.

There accordingly remains a continuing need for cost-effective, efficient, and environmentally friendly methods for the selective oxidation of primary and secondary alcohols to their corresponding aldehydes and ketones.

SUMMARY

A method of oxidizing alcohols comprises reacting an alcohol with oxygen in the presence of an effective amount of a manganese-containing octahedral molecular sieve or a manganese-containing octahedral layer material.

A preferred manganese-containing octahedral molecular sieve has the formula

$$A_{2-y}Mn_8O_{16} \cdot xH_2O$$

wherein A is $H^+$, $Na^+$, or $K^+$, y is about 0.5 to about 1.5, and x is 0 to about 20.

Another preferred manganese-containing octahedral molecular sieve has the formula

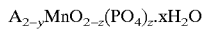

$$A_{2-y}MnO_{2-z}(PO_4)_z \cdot xH_2O$$

wherein A is $H^+$, $Na^+$, or $K^+$, y is preferably about 0.5 to about 1.5, z is greater than zero to two, and x is 0 to about 20.

Still another preferred manganese octahedral material is a co-synthesized mixture of gamma-manganese oxide and one of the above-described manganese-containing octahedral molecular sieves.

DESCRIPTION OF THE FIGURES

FIG. 1 illustrates the shape selectivity of the present oxidation using three benzenedimethanol isomers.

FIG. 2 illustrates the site-selective oxidation of dihydroxyarenes.

DESCRIPTION OF THE PREFERRED EMBODIMENTS AND BEST MODE

Figure 3:
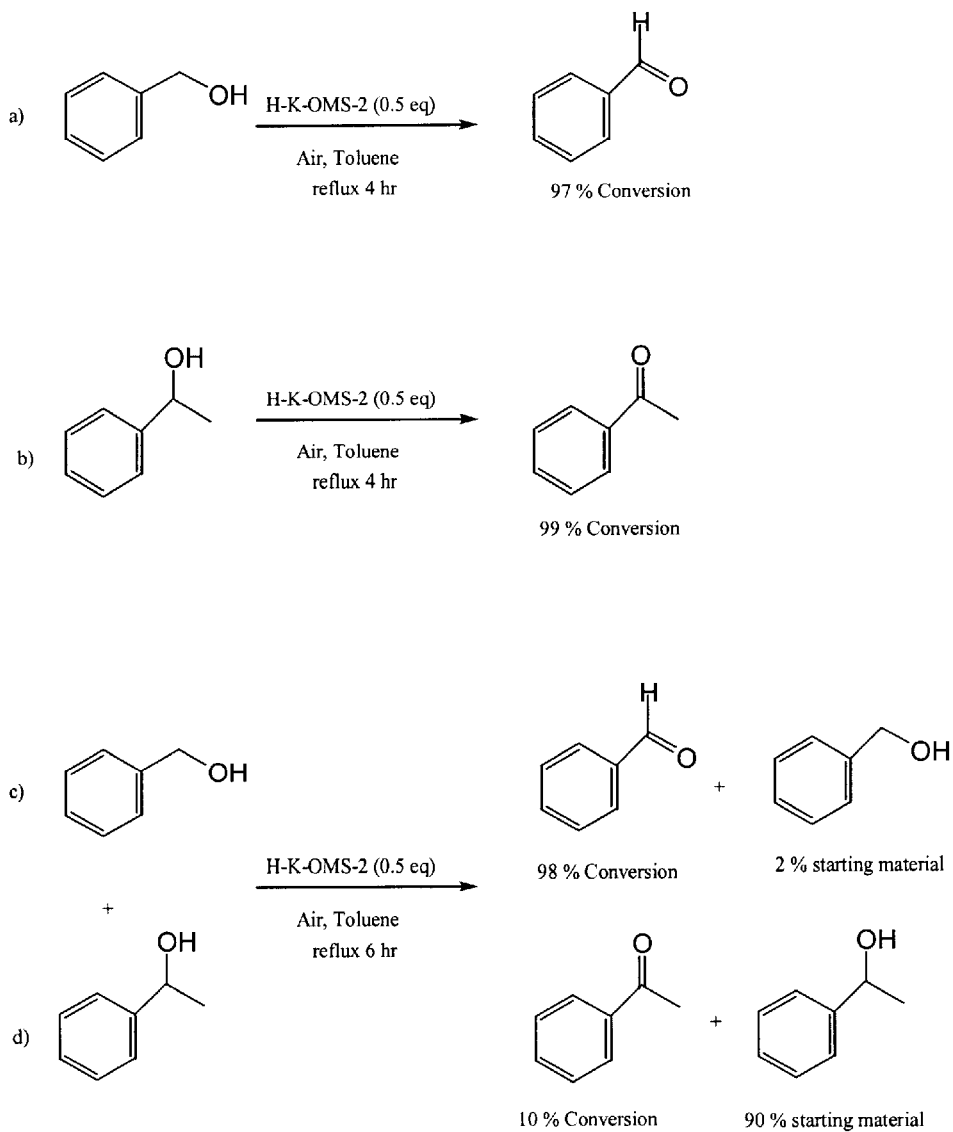
FIG. 3 illustrates the results of individual and competitive reaction of benzyl alcohol and sec-phenethyl alcohol.

An efficient, selective method for the oxidation of alcohols uses mangansese-containing octahedral materials, including octahedral molecular sieves and octahedral layer (OL) materials. Use of such materials allows efficient, and selective oxidation of primary alcohols to aldehydes, and secondary alcohols to ketones. Spatial selectivity (i.e., selective oxidation of one alcohol in the presence of another alcohol on the same molecule) is also possible.

A preferred manganese-containing octahedral molecular sieve may be represented by the formula

$$A_{2-y}Mn_8O_{16} \cdot xH_2O$$

wherein A is $H^+$, $Na^+$, or $K^+$, y is preferably about 0.5 to about 1.5, and x is 0 to about 20. In a preferred embodiment, A is a mixture of $K^+$ and $H^+$. These materials consist of structural units of $MnO_6$ octahedra, which are edge and corner shared, and which contain 4.6 Å×4.6 Å tunnels due to a 2×2 arrangement of octahedra. They are conveniently referred to as "OMS-2 catalysts".

Specific OMS-2 catalysts include potassium cryptomelane octahedral molecular sieves ("K-OMS-2", also known as hollandite), which is a microporous manganese oxide with a composition of $KMn_8O_{16} \cdot nH_2O$. Potassium ions are present in the tunnels with a small amount of water. The average manganese oxidation state of 3.8 of K-OMS-2 is due to a mixture of $Mn^{4+}$, $Mn^{3+}$, and $Mn^{2+}$. Pore size distributions studies show that a broad range of micropores are present, ranging from about 4.5 to about 7 Å.

Substitution of at least some of the potassium ions with hydrogen may be achieved by treatment of K-OMS-2 with a mineral acid such as $HNO_3$, yielding a catalyst wherein A is $H^+$ and $K^+$ ("H-K-OMS-2"). Sodium cryptomelane octahedral molecular sieves ("Na-OMS-2") may also be used as an oxidative catalyst. Advantageously, the OMS-2 materials are very stable and can be stored for a long time (activity retained after 2 years). They are also thermally stable up to 700° C. in oxygen.

Another type of effective octahedral manganese molecular sieve comprises phosphate, has the formula

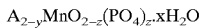

$$A_{2-y}MnO_{2-z}(PO_4)_z \cdot xH_2O$$

wherein A is $H^+$, $Na^+$, or $K^+$, y is preferably about 0.5 to about 1.5, z is greater than zero to about 2, and x is 0 to about 20. A specific example of this type of phosphate-containing octahedral molecular sieve has the formula $Na_{0.437}MnO_{1.764}(PO_4)_{0.236} \cdot xH_2O$ ("MPOS-5") was synthesized in powder form. The average oxidation state of manganese was determined to be $3.86^+$ by a titration method. MPOS-5 is thermally stable up to 520° C. Porosity studies indicate that MPOS-5 is a microporous material with a surface area as high as 133 $m^2/g$.

Still another preferred manganese octahedral material is a co-synthesized mixture of gamma-manganese oxide and one of the above-described manganese-containing octahedral molecular sieves or layer materials. For example, it has been found that gamma-manganese oxide may be co-synthesized together with Na-OMS-2. The oxidative activity of the co-synthesized gamma-Na-OMS-2 catalyst differs from a mechanical mixture of Na-OMS-2 and gamma-$MnO_2$, in that the synthesized mix-phased materials demonstrate superior catalytic activity in partial oxidation of benzylic alcohol to aldehyde compared to the mechanical mixture.

On a macroscopic level, octahedral manganese molecular sieves and layer materials may exist as powders, thin films, strands, helices, and rings. These materials and their preparation are described more fully, for example, in U.S. Pat. Nos. 5,340,562 and 5,695,618 to O'Young et al., and U.S. application Ser. No. 09/624,423 to Suib, et al., filed Jul. 24, 2000.

Oxidation of a primary or secondary alcohol with oxygen in the presence of a manganese-containing molecular sieve, for example an OMS-2 catalyst, can be generally represented as

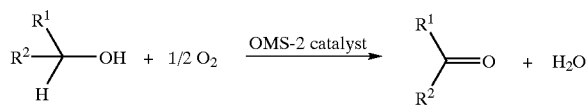

wherein $R^1$ is a substituted or unsubstituted $C_{1-36}$ alkyl or cycloalkyl, substituted or unsubstituted $C_{1-36}$ alkenyl or cycloalkenyl, substituted or unsubstituted $C_{6-36}$ aryl, substituted or unsubstituted $C_{5-36}$ heteroaryl, substituted, unsubstituted, saturated, unsaturated, or aromatic $C_{3-36}$ heterocycle, or the like; $R^2$ is hydrogen, a substituted or unsubstituted $C_{1-36}$ alkyl or cycloalkyl, substituted or unsubstituted $C_{1-36}$ alkenyl or cycloalkenyl, substituted or unsubstituted $C_{1-36}$ aryl, or substituted, unsubstituted, saturated, unsaturated, or aromatic $C_{3-36}$ heterocycle, or the like; or $R^1$ and $R^2$ taken together form a substituted or unsubstituted $C_{1-36}$ cyclic group, a substituted or unsubstituted $C_{6-36}$ aromatic cyclic group, or a substituted or unsubstituted, saturated, unsaturated, or aromatic $C_{3-36}$ heterocyclic group, or the like. As used herein "cyclic" is intended to encompass groups having one or more rings, e.g., phenyl groups, biphenyl groups, and napthyl groups.

Preferably, $R^1$ is a substituted or unsubstituted $C_{1-18}$ alkyl, substituted or unsubstituted $C_{1-18}$ alkenyl, substituted or unsubstituted $C_{6-18}$ aryl, substituted or unsubstituted, $C_{3-8}$ heterocycle, or the like; $R^2$ is hydrogen or a substituted or unsubstituted $C_{1-18}$ alkyl, substituted or unsubstituted $C_{1-18}$ alkenyl, or substituted or unsubstituted $C_{1-18}$ aryl; or $R^1$ and $R^2$ taken together form a substituted or unsubstituted $C_{1-18}$ cyclic group, a substituted or unsubstituted $C_{6-18}$ aromatic cyclic group, or a substituted or unsubstituted, saturated or aromatic $C_{3-18}$ heterocyclic group.

Preferably, $R^2$ is hydrogen, a substituted or unsubstituted $C_{1-8}$ alkyl, or substituted or unsubstituted $C_{1-8}$ alkenyl. Even more preferably, $R^1$ is benzylic or allylic, and $R^2$ is hydrogen, methyl, ethyl, or propyl.

There is no particular limitation on the substituents that may be present on the alkyl, alkenyl, aryl and heteroaryl groups above, so long as they do not interfere with the oxidation. Exemplary substitutions may include, but are not limited to, halogen, hydroxy, alkoxy, amino, alkylamino, arylamino, aldehyde, carboxylato, carbonamido, sulfonamido, carbamoyl, sulfamoyl, sulfonato, alkoxycarbonyl, aryloxycarbonyl, acyloxy, alkylsulfonyl, arylsulfonyl, sulfonyloxy, alkylthio, alkyl, alkenyl, aryl, heteroaryl, or heterocycle.

Specific examples of suitable alcohols include aliphatic alcohols, such as isopropanol, 2-butanol, and cyclophenanol; benzylic alcohols such as benzyl alcohol, 4-chlorobenzyl alcohol, 4-methylbenzyl alcohol, benzhydrol, and sec-phenylethyl alcohol; and allylic alcohols such as cinnamyl alcohol, geraniol, 2-cyclohexen-1-ol, and 2-thiophenemethanol. Benzoins having the formula Ar—CH(OH)—C(O)—Ar, wherein Ar is phenyl, p-methoxyphenyl, furyl, or pyridinyl are converted to the corresponding benzil compounds having the formula Ar—C(O)—C(O)—Ar in greater than 90% yield with 100% selectivity.

While a stoichiometric or excess amount of the OMS-2 catalyst can be used, for example, up to a 10-fold excess based on the ratio of atomic manganese to alcohol groups, it is preferred to use a catalytically effective amount of the OMS-2 catalyst. For example, the amount of manganese oxide may be about 1 mole percent to about 90 mole percent, preferably about 5 to about 50 mole percent, based on manganese atoms and alcohol groups.

One of the key advantages of the method is that the stoichiometric oxidant is molecular oxygen, which can be supplied as air or oxygen. The oxygen or air may be simply introduced via a bubbler at a pressure up to about one atmosphere, or higher pressures may be employed. In the oxidation of cinnamyl alcohol with K-OMS-2, use of air resulted in 50% conversion to the corresponding aldehyde after 4 hours under reflux, while use of oxygen resulted in 80% conversion after 4 hours under reflux. While gaseous oxygen as the oxidant is preferred for simplicity and economy, it is expressly contemplated to utilize other oxygen oxidants including hydrogen peroxide, and organic peroxides, including tbutylhydroperoxide, and the like.

While there is no particular limitation on reaction temperature, typical reaction temperatures are about 25° C. to about 150° C.

The alcohol may be oxidized neat or in the presence of a solvent. Use of a solvent is presently preferred, as its selection according to boiling point allows a simple means of controlling the reaction temperature. Suitable solvents do not substantially interfere with the oxidation and may be readily determined by those of ordinary skill in the art, depending on solubility of the alcohol, boiling point, cost, and similar considerations. Suitable solvents having boiling points within the range of about 25° C. to about 150° C. include but are not limited to xylene, toluene, n-hexane, tetrahydrofuran, water, diethyl ether, acetonitrile, and the like, as well as mixtures comprising at least one of the foregoing solvents.

Methods commonly used to provide heat to a liquid and to a vapor-liquid mixture can be utilized, including electrical resistance, microwave heating, radio-frequency inductive heating, and the like.

It is preferred to agitate the reaction mixture. For example, it has been observed that reaction rates are higher with stirring than without.

It was observed that the addition of base or doping materials such as $Cr^{3+}$, $Ni^{2+}$, or $Co^{2+}$ to K-OMS-2 catalyzed oxidations decreased the conversion. Use of H-K-OMS-2 significantly enhanced conversions, as shown in Table 1 below. Use of H-K-OMS-2 in the oxidation of cinnamyl alcohol resulted in a 95% conversion with 100% selectivity, while oxidation of cinnamyl alcohol with K-OMS-2 in the presence of a small amount of mineral acids (e.g., 0.2 mL of $HNO_3$ to a standard reaction as described in Example 1) resulted in a 100% conversion with only 65% selectivity. Alkyl alcohols were converted in higher yields when very small amounts of mineral acids were used as co-catalysts. These results suggest that OMS-2 catalyzed alcohol oxidations are accelerated by Brönsted acids.

Water, which is the only side product produced from the oxidation reaction, poisons the octahedral manganese oxide molecular sieve catalyst. The catalyst can also physically absorb the aldehydes formed in the reaction. After the oxidation reaction, the filtered octahedral manganese oxide molecular sieve catalyst may be washed with methanol and water and heated to 300° C., and becomes reusable as a catalyst without any appreciable loss of activity for oxidation. XRD and IR studies indicated that after being heated to 300° C. the catalyst returned to its original composition and structure. Temperature programmed desorption studies of used catalysts shows only desorption of $H_2O$, reactant, or product.

The kinetics of the oxidation were investigated and the reaction appears to follow a Mars-van Krevelen type of oxidation mechanism. The proposed mechanism indicates a multi-electron redox event occurring in the liquid phase.

A particularly advantageous feature of the oxidative method is shape selectivity, as illustrated by the oxidation of three benzenedimethanol isomers as shown in FIG. 1 (Example 6 below). Oxidation of 1,2-benzenedimethanol resulted in very low conversion, yielding a mixture of phthalide, phthalaldehyde, and 2-(hydroxymethyl) benzaldehyde (a mono-oxidized product). Oxidation of 1,3-benzenedimethanol yielded only the mono-oxidized product 3-(hydroxymethyl)benzaldehyde. Oxidation of 1,4-benzenedimethanol yielded terephthalaldehyde. These results show that the H-K-OMS-2 catalyst gives shape selective reaction products.

Shape selectivity is also illustrated by the oxidation of di-hydroxyarenes with H-K-OMS-2 (FIG. 2), wherein only linear hydroquinone (which presumably can fit in the tunnels of the catalyst) gave a high conversion. Catechol and resorcinol did not react. In another experiment, it was shown that the oxidation of benzyl alcohol with H-K-OMS-2 resulted in 97% conversion, while oxidation of a large, bulky molecule such as 1-acenaphthenol results in only 5% conversion.

Finally, in the individual reaction of either benzyl alcohol or sec-phenethyl alcohol, each substrate gave more than 95% conversion. However, in competitive reactions using both two substrates simultaneously, only benzyl alcohol was converted into benzaldehyde in 6 hours, with 98% conversion and 100% selectivity (FIG. 3). Oxidation of sec-phenethyl alcohol gave just 10% conversion to acetophenone. After refluxing for 20 h, sec-phenethyl alcohol formed acetophenone with 30% conversion. Benzyl alcohol, which is a relatively good fit to the H-K-OMS-2 tunnels, is completely converted to benzaldehyde. The sec-phenethyl alcohol, on the other hand, is larger with a more sterically hindered hydroxylic carbon and is left mostly unreacted.

As the successful oxidation of thiophenemethanol shows, another advantage of this method that an alcohol may be selectively oxidized in the presence of other oxidizable functional groups such as sulfides. Geraniol gave geranial without any isomerization. Alpha-unsaturated alcohols, such as benzylic alcohols and allylic alcohols, are oxidized more rapidly than alcohols lacking alpha-unsaturation.

In another important feature, over oxidation was not observed with the octahedral manganese oxide molecular sieve catalysts, i.e., benzyl alcohol may be oxidized to benzaldehyde in greater than 90% yield with any one of K-OMS-2, K-H-OMS-2, Na-OMS-2, or MPOS-5, with no observed oxidation to benzoic acid. MPOS-5 catalyzes the selective oxidation of benzylic alcohols to aldehydes by air with 65% conversion and 100% selectivity in 4 hours, whereas it was found that the OMS-2 materials gave about 55% conversion with 100% selectivity in 4 hours.

The method can be carried out under mild conditions, exhibits high selectivity, and utilizes an environmentally friendly catalyst. The method overcomes disadvantages associated with previous manganese oxide oxidations, which required stoichiometric quantities of manganese oxide and exhibited highly variable activity depending on the method of preparation and storage of the manganese oxide catalyst. The method also avoids the expense associated with oxidation catalysts based on precious metals such as ruthenium, platinum, and rhodium, and does not require the presence of a co-reactant other than an oxygen source.

The method is further illustrated by the following non-limiting examples. All of the references cited herein are incorporated by reference hereby.

Preparation and Characterization of OMS-2 Catalysts

The preparation of synthetic cryptomelane (K-OMS-2) is as follows: 225 mL of potassium permanganate solution (0.4 M) was added to a 500 mL round-bottomed flask containing a mixture of 67.5 mL of manganese sulfate hydrate solution (1.75 M) and 6.8 mL concentrated nitric acid. The dark brown slurry was stirred under reflux for 24 hours, then filtered and washed with deionized water several times. The catalyst was dried at 120° C. overnight before use.

The preparation of H-K-OMS-2 was as follows: nitric acid (1 M, 50 mL) was added to a 100 mL round bottom flask. $K^+$-OMS-2 (2.5 g) was added to the flask, and the mixture was heated to about 60° C. to about 70° C. with vigorous stirring for between 3 and 20 hours. The solid was filtered, washed with deionized water several times (until a neutral pH was achieved), and dried in an oven at 120° C. for about 3 to about 20 hours. Elemental analysis gave the formula $H_{0.2}K_{0.8}Mn_8O_{16} \cdot nH_2O$, indicating about 20% ion exchange.

The surface area of both K-OMS-2 and H-K-OMS-2 was measured by the Brunauer-Emmett-Teller (BET) method on a Micromeritics ASAP 2010 instrument. The measurements were made using $N_2$ gas as the adsorbent and a multi-point method. The surface area of K-OMS-2 was found to be about 97 $m^2g^{-1}$, while that of H-K-OMS-2 was found to be about 85 $m^2g^{-1}$.

Both the K-OMS-2 and H-K-OMS-2 catalysts were characterized by XRD methods. Data was collected using a Scintag 2000 PDS instrument with Cu Kα radiation, a beam voltage of 45 kV and 40 mA beam current. The structure was verified by comparing with standards and it was conserved even after ion exchange.

Preparation of MPOS-5 Catalysts

Manganese sulfate was added to $(NaPO_3)_6$ and then mixed with $NaMnO_4$. After mixing, tetraethylammonium bromide and butanol were added to the mixture, which was then aged at room temperature for 3 weeks and then put in an autoclave for 7 days at 150° C. After cooling, the catalyst was filtered, washed with distilled, deionized water, and dried.

Preparation of Gamma-Na-OMS-2 and Gamma-H-Na-OMS-2 Catalysts p Gamma-Na-OMS-2 was prepared by refluxing method. In a 500 mL round-bottom flask fitted with a condenser, 225 mL of a sodium permanganate hydrate solution ($NaMnO_4 \cdot H_2O$, 0.4 M) was added to a mixture of 67.5 mL of manganese sulfate solution (1.75 M) and 6.8 mL concentrated nitric acid. The dark-brown slurry was stirred under reflux for 24 hours, then filtered, and washed with distilled, deionized water. The catalyst was then dried at 120° C. overnight before use.

The preparation of gamma-H-Na-OMS-2 is as follows. Gamma-Na-OMS-2 was stirred in a 1 M solution of nitric acid for several hours at about 60 to about 70° C., forming gamma-H-Na-OMS-2. After the same washing and drying procedure, the catalyst was ready for use.

EXAMPLE 1

A typical procedure for the alcohol oxidation reaction is as follows: toluene (10 mL) and the alcohols (1 mmol) were first added to a 50-mL round-bottomed flask containing 0.05 g of the octahedral manganese oxide molecular sieve catalyst (about 0.5 eq, wherein one manganese is considered as one active site). The mixture was then stirred under reflux (110° C.) in air. After 4 hours, the reaction mixture was cooled, the catalyst was removed by filtration, and the filtrate was analyzed using GC/MS, $^1$H NMR, and IR. The GC-MS analyses were done using a HP 5890 series II chromatograph with a thermal conductivity detector coupled with a HP 5970 mass selective detector. The column used was a HP-1 (cross-linked methyl siloxane) with dimensions of 12.5 m×0.2 m×0.33-micrometer film thickness.

EXAMPLE 2

Table 1 below illustrates the percent conversion of various alcohols oxidized by octahedral manganese oxide molecular sieve catalysts at 110° C. under toluene reflux in air for 4 hours using the above procedure. The selectivity of all oxidation reactions was 100%. Percent conversion was measured by gas chromatography and $^1$H NMR using an internal standard.

TABLE 1

| Entry | Substrate | Product | Catalyst | Conversion (%) |
|---|---|---|---|---|
| 1 | benzyl alcohol | benzaldehyde | K—OMS-2<br>H—K—OMS-2 | 90<br>97 |
| 2 | 1-phenylethanol | acetophenone | K—OMS-2<br>H—K—OMS-2 | 93<br>99 |
| 3 | 4-chlorobenzyl alcohol | 4-chlorobenzaldehyde | K—OMS-2<br>H—K—OMS-2 | 95<br>99 |
| 4 | cinnamyl alcohol | cinnamaldehyde | K—OMS-2<br>H—K—OMS-2 | 50<br>95 |
| 5 | 2-thiophenemethanol | 2-thiophenecarboxaldehyde | K—OMS-2<br>H—K—OMS-2 | 40<br>100 |
| 6 | benzhydrol | benzophenone | K—OMS-2<br>H—K—OMS-2 | 35<br>100 |
| 7 | geraniol | citral | K—OMS-2<br>H—K—OMS-2 | 5<br>95 |
| 8 | 2-cyclohexen-1-ol | 2-cyclohexen-1-one | K—OMS-2<br>H—K—OMS-2 | 30<br>90 |

TABLE 1-continued

| Entry | Substrate | Product | Catalyst | Conversion (%) |
|---|---|---|---|---|
| 9 | cyclopentanol (OH) | cyclopentanone (O) | K—OMS-2<br>H—K—OMS-2 | 35[a]<br>67[a] |

[a]Reaction time was 20 hours.

EXAMPLE 3

This example illustrates the oxidation of benzyl alcohol using conventional thermal heating and microwave heating. Benzyl alcohol was oxidized using K-OMS-2 catalyst using the procedure of Example 3 without stirring, except that the reaction mixture was heated for only 10 minutes. A 38% conversion of starting material with 100% selectivity was achieved. The same reactants were heated via microwave for 10 minutes with temperature controlled to 110° C., achieving a 58% conversion of starting material with 100% selectivity. This examples shows that microwave heating can be used to reduce reaction times without sacrificing selectivity.

EXAMPLE 4

To determine shape selectivity of the oxidation of alcohols, the following general procedures were used. In a 50 mL, 2-neck round-bottomed flask fitted with a reflux condenser, 0.05 g (about 0.5 mmol) of H-K-OMS-2 catalyst and dimethylsulfoxide (DMSO) (0.5 mL) was added, followed by 1 mmol of the reacting alcohol and 10 mL of toluene as the solvent. Air was bubbled in from the side-neck. The reaction mixture is heated in an oil-bath for 4 h and the catalyst removed by filtration. The filtrate was analyzed using a GC-MS, $^1H$ NMR, $^{13}C$ NMR, and IR. Results are illustrated in FIG. 1.

EXAMPLE 5

To determine the effect of acid co-catalysts, oxidations were conducted on cyclohexanol as described in example 1 using H-K-OMS-2 under reflux for 20 hours, except that 0.5 mL of acetic acid, nitric acid, hydrochloric acid, or a solid acid such as phosphomolybdic acid or phosphotungstic acid were added to each reaction. Yields of cyclohexanone were 100% where nitric acid was added, 18% for hydrochloric acid, 10% for acetic acid, and 10% for solid acid.

In a similar reaction using 0.5 equivalents of H-K-OMS-2 in a 1:1 by weight mixture of H-K-OMS-2 and a strongly acidic sulfonated ion exchange resin (DOWEX-50W-H$^+$) co-ground and dried at 100° C. for 2 days, cyclohexanol was converted to cyclohexanone and cyclohexene in a 100% yield, with 50% selectivity.

EXAMPLE 6

In order to characterize the partial oxidation of benzylic alcohol to benzylic aldehyde using air in the presence of Na-OMS-2, toluene was used as the solvent. The catalytic reaction was carried out by refluxing the alcohol and Na-OMS-2 (about 0.5 equivalents with respect to the alcohol) at 110° C. in a glass flask with aeration. The alcohol to solvent (toluene) ratio is usually 1:100. Superior selectivity, 100% is achieved. Conversion increases with time, 55% after reflux at 110° C. for 4 hours, 75% after 8 hours, and 90% after 20 hours. The Na-OMS-2 catalysts can be re-used many times. The Na-OMS-2 has a similar initial conversion compared with other conventional OMS-2 materials, such as K-OMS-2, but higher steady state conversion. The catalytic conversion of the Na-OMS-2 can reach 90% in 20 hours, while the catalytic conversion of K-OMS-2 can reach about 75% with even a longer time. The unique mesoporous property of the Na-OMS-2 may play a role in this improved catalytic activity.

EXAMPLE 7

The oxidative activity of the gamma-Na-OMS-2 catalyst as prepared above differs from a mechanical mixture of Na-OMS-2 and gamma-MnO$_2$, in that the synthesized mix-phased materials demonstrate superior catalytic activity in partial oxidation of benzylic alcohol to aldehyde compared to the mechanical mixture. The synthesized mixed phase materials were found to effect 95% conversion of benzyl alcohol to the aldehyde with 100% selectivity in 4 hours at 110° C., which is similar to the activity observed for H-K-OMS-2.

EXAMPLE 8

A summary of the results of oxidation of various alcohols using gamma-H-Na-OMS-2 (compared with (Bi(NO$_3$)$_3$, the bismuth catalyst not being a part of the present invention) is shown in Table 2 below:

TABLE 2

Ar-CH(OH)-Ar' →(gamma-H—Na—OMS-2, Toluene, reflux, 20 h)→ Ar-C(O)-C(O)-Ar'

| | | Yield (%)* | |
|---|---|---|---|
| Ar | Ar' | Bi(NO$_3$)$_3$.5H$_2$O | gamma-H—Na—OMS-2 |
| Ph | Ph | 99 | 99 |
| p-MeOC$_6$H$_4$ | p-MeOC$_6$H$_4$ | 99 | 99 |
| 2-furyl | 2-furyl | 58 | 99 |

TABLE 2-continued

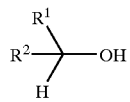
Ar  Ar' gamma-H—Na—OMS-2
Toluene, reflux, 20 h
⟶

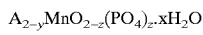

| | | Yield (%)* | |
|---|---|---|---|
| Ar | Ar' | Bi(NO$_3$)$_3$·5H$_2$O | gamma-H—Na—OMS-2 |
|  | | 10 | 99 |

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method of oxidizing a primary or secondary organic alcohol, comprising:
   contacting the primary or secondary organic alcohol with a stoichiometric excess of oxygen in the presence of an effective amount of a manganese-containing octahedral molecular sieve or a manganese-containing octahedral layer material.

2. The method of claim 1, wherein the manganese-containing octahedral molecular sieve has the formula $$A_{2-y}Mn_8O_{16}\cdot xH_2O$$

where A is H$^+$, Na$^+$, or K$^+$, y is about 0.5 to about 1.5, and x is 0 to about 20, or the formula $$A_{2-y}MnO_{2-z}(PO_4)_z\cdot xH_2O$$

wherein A is H$^+$, Na$^+$, or K$^+$, y is about 0.5 to about 1.5, z is greater than zero to about 2, and x is 0 to about 20.

3. The method of claim 1, wherein the manganese-containing octahedral molecular sieve has the formula $A_{2-y}Mn_8O_{16}\cdot xH_2O$ and A is H$^+$, K$^+$, or a mixture thereof.

4. The method of claim 1, wherein the manganese-containing octahedral molecular sieve has the formula $A_{2-y}MnO_{2-z}(PO_4)_z\cdot xH_2O$ wherein A is Na$^1$, y is 1.563 and z is 0.236.

5. A method of oxidizing a primary or secondary organic alcohol, comprising:
   contacting the primary or secondary organic alcohol with a stoichiometric excess of oxygen in the presence of an effective amount of a manganese-containing octahedral molecular sieve or a manganese containing octahedral layer material;
   wherein the manganese-containing octahedral molecular sieve is co-synthesized to comprise gamma-manganese dioxide.

6. A method of oxidizing a primary or secondary organic alcohol, comprising:
   contacting the primary or secondary organic alcohol with a stoichiometric excess of oxygen in the presence of an effective amount of a manganese-containing octahedral molecular sieve or a manganese-containing octahedral layer material;
   wherein the manganese-containing octahedral molecular sieve is co-synthesized to comprise gamma-manganese dioxide and has the formula $$A_{2-y}Mn_8O_{16}\cdot xH_2O$$

wherein A is H$^+$, Na$^+$, or K$^+$, y is about 0.5 to about 1.5, and x is 0 to about 20.

7. The method of claim 1, wherein the alcohol has the formula $$R^2 \overset{R^1}{\underset{H}{-}} OH$$

wherein R$^1$ is a substituted or unsubstituted C$_{1-36}$ alkyl or cycloalkyl, substituted or unsubstituted C$_{1-36}$ alkenyl or cycloalkenyl, substituted or unsubstituted C$_{6-36}$ aryl, substituted or unsubstituted C$_{5-36}$ heteroaryl, substituted, unsubstituted, saturated, unsaturated, or aromatic C$_{3-36}$ heterocycle; R$^2$ is hydrogen, a substituted or unsubstituted C$_{1-36}$ alkyl or cycloalkyl, substituted or unsubstituted C$_{1-36}$ alkenyl or cycloalkenyl, substituted or unsubstituted C$_{1-36}$ aryl, or substituted, unsubstituted, saturated, unsaturated, or aromatic C$_{3-36}$ heterocycle; or R$^1$ and R$^2$ taken together form a substituted or unsubstituted C$_{1-36}$ cyclic group, a substituted or unsubstituted C$_{6-36}$ aromatic cyclic group, or a substituted or unsubstituted, saturated, unsaturated, or aromatic C$_{3-36}$ heterocyclic group, wherein the substitutions are halogen, hydroxy, alkoxy, amino, alkylamino, arylamino, aldehyde, carboxylato, carbonamido, sulfonamido, carbamoyl, sulfamoyl, sulfonato, alkoxycarbonyl, aryloxycarbonyl, acyloxy, alkylsulfonyl, arylsulfonyl, sulfonyloxy, alkylthio, alkyl, alkenyl, aryl, heteroaryl, heterocycle, or a combination thereof.

8. The method of claim 7, wherein R$^1$ is a substituted or unsubstituted C$_{1-18}$ alkyl, substituted or unsubstituted C$_{1-18}$ alkenyl, substituted or unsubstituted C$_{6-18}$ aryl, substituted or unsubstituted, C$_{3-18}$ heterocycle; R$^2$ is hydrogen or a substituted or unsubstituted C$_{1-18}$ alkyl, substituted or unsubstituted C$_{1-18}$ alkenyl, or substituted or unsubstituted C$_{1-18}$ aryl; or R$^1$ and R$^2$ taken together form a substituted or unsubstituted C$_{1-18}$ cyclic group, a substituted or unsubstituted C$_{6-18}$ aromatic cyclic group, or a substituted or unsubstituted, saturated or aromatic C$_{3-18}$ heterocyclic group.

9. The method of claim 8, wherein R$^2$ is hydrogen, a substituted or unsubstituted C$_{1-8}$ alkyl, or substituted or unsubstituted C$_{1-8}$ alkenyl.

10. The method of claim 7, wherein the organic alcohol is benzoin, a benzylic alcohol, or an allylic alcohol.

11. The method of claim 7, wherein the organic alcohol is an aliphatic alcohol.

12. The method of claim 1, wherein the moles of manganese atoms in the catalyst is present at about 1 to about 50 mole percent relative to the organic alcohol.

13. The method of claim 1, wherein the organic alcohol is contacted with oxygen at a temperature of about 25° C. to about 150° C.

14. The method of claim 1, wherein oxygen is supplied as air.

15. The method of claim 1, wherein the oxidation is conducted in a solvent.

16. A method of oxidizing an organic alcohol, comprising:

in a solvent, contacting a primary or secondary cycloaliphatic, allylic, or benzylic alcohol with a stoichiometric excess of oxygen in the presence of a manganese-containing octahedral molecular sieve having a one-dimensional tunnel structure, wherein the molecular sieve is present in an amount effective to oxidize the primary cycloalphatic, allylic, or benzylic alcohol to an aldehyde or the secondary cycloaliphatic, allylic, or benzylic alcohol to a ketone.

17. The method of claim 1, wherein the oxidation is conducted in the liquid phase.

18. The method of claim 7, wherein at least one of $R^1$ and $R^2$ comprises a hydroxy substituent.

19. A method of oxidizing a primary or secondary organic alcohol, comprising:

contacting the primary or secondary organic alcohol with a stoichiometric excess of oxygen in the presence of an effective amount of an manganese-containing octahedral molecular sieve having the formula

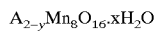

wherein A is $H^+$, $Na^+$, or $K^+$, y is about 0.5 to about 1.5, and x is 0 to about 20.

20. The method of claim 19, wherein the manganese-containing octahedral molecular sieve is co-synthesized to comprise gamma-manganese dioxide.

21. The method of claim 19, wherein the alcohol has the formula

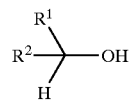

wherein $R^1$ is a substituted or unsubstituted $C_{1-36}$ alkyl or cycloalkyl, substituted or unsubstituted $C_{1-36}$ alkenyl or cycloalkenyl, substituted or unsubstituted $C_{6-36}$ aryl, substituted or unsubstituted $C_{5-36}$ heteroaryl, substituted, unsubstituted, saturated, unsaturated, or aromatic $C_{3-36}$ heterocycle; $R^2$ is hydrogen, a substituted or unsubstituted $C_{1-36}$ alkyl or cycloalkyl, substituted or unsubstituted $C_{1-36}$ alkenyl or cycloalkenyl, substituted or unsubstituted $C_{1-36}$ aryl, or substituted, unsubstituted, saturated, unsaturated, or aromatic $C_{3-36}$ heterocycle; or $R^1$ and $R^2$ taken together form a substituted or unsubstituted $C_{1-36}$ cyclic group, a substituted or unsubstituted $C_{6-36}$ aromatic cyclic group, or a substituted or unsubstituted, saturated, unsaturated, or aromatic $C_{3-36}$ heterocyclic group, wherein the substitutions are halogen, hydroxy, alkoxy, amino, alkylamino, arylamino, aldehyde, carboxylato, carbonamido, sulfonamido, carbamoyl, sulfamoyl, sulfonato, alkoxycarbonyl, aryloxycarbonyl, acyloxy, alkylsulfonyl, arylsulfonyl, sulfonyloxy, alkylthio, alkyl, alkenyl, aryl, heteroaryl, heterocycle, or a combination thereof.

22. The method of claim 19, wherein the oxidation is conducted in a solvent.

23. The method of claim 19, wherein the oxidation is conducted in the liquid phase.

* * * * *

UNITED STATES PATENT AND TRADEMARK OFFICE
CERTIFICATE OF CORRECTION

PATENT NO. : 6,486,357 B2
APPLICATION NO. : 09/929302
DATED : November 26, 2002
INVENTOR(S) : Steven L. Suib et al.

Page 1 of 1

It is certified that error appears in the above-identified patent and that said Letters Patent is hereby corrected as shown below:

Title Page:
Item (56), References Cited, Other Publications, Column 2, Line 26, after "with", insert --a--.
Item (56), References Cited, Other Publications, Column 2, Line 32, after "Total", delete "oxidationsof" and insert therefor --oxidations of--.

Column 4,
Line 21, after "including", delete "tbutylhydroperoxide" and insert therefor --t-butylhydroperoxide--.

Column 6,
Line 47, after "catalysts", delete "p".

Column 11,
Line 54, after "1.563", insert --,--.

Column 12,
Line 10, delete "$A_{2-y}Mn_8O_{16} . xH_2O$" and insert therefor --$A_{2-y}Mn_8O_{16} . xH_20$--.

Column 13,
Line 21, after "of", delete "an" and insert therefor --a--.

Signed and Sealed this

Seventeenth Day of April, 2007

JON W. DUDAS
*Director of the United States Patent and Trademark Office*